Figure 1:
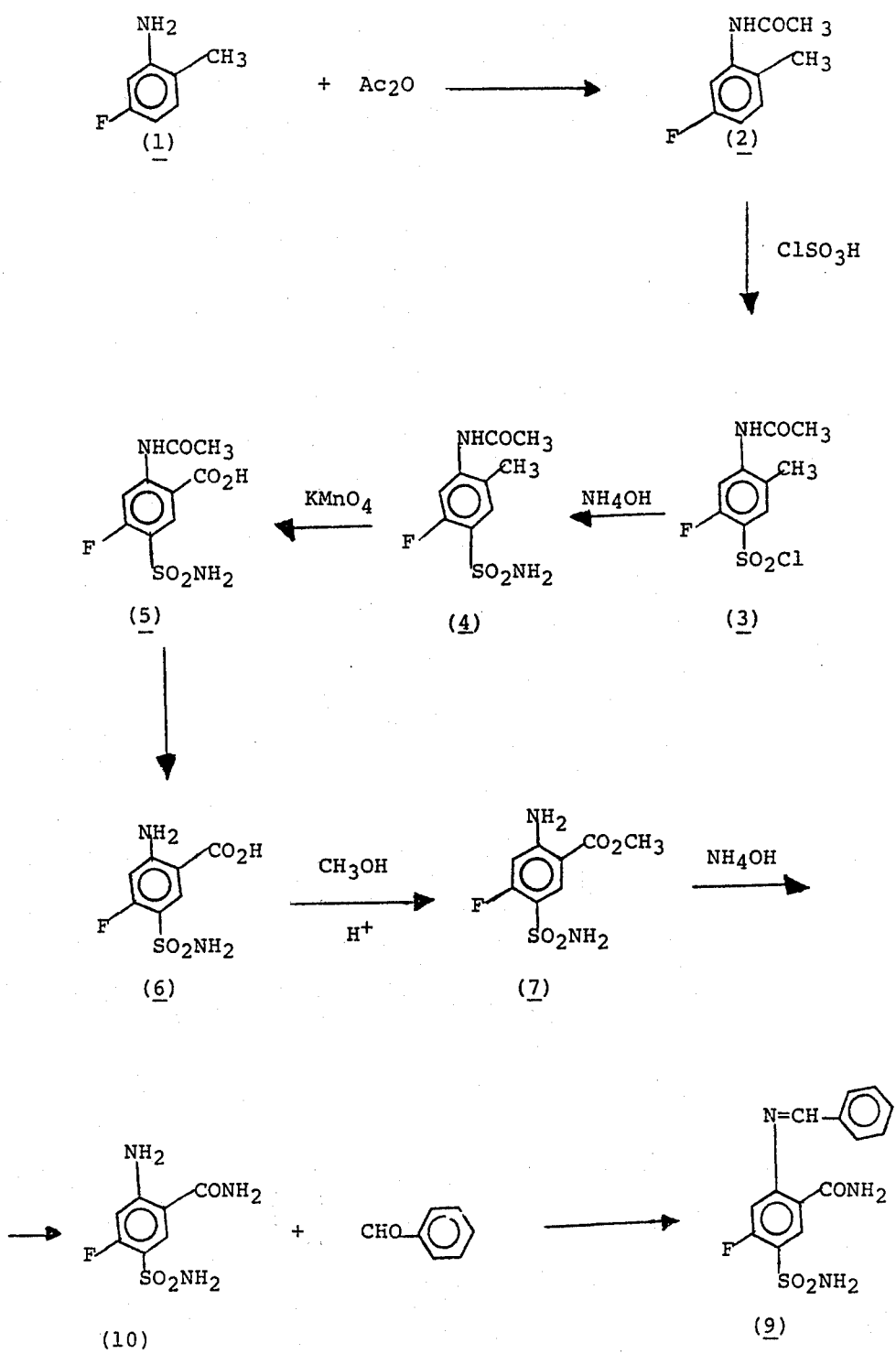

United States Patent [19]

Purcell et al.

[11] 4,312,862
[45] Jan. 26, 1982

[54] THERAPEUTICALLY ACTIVE DERIVATIVES OF BENZAMIDE

[75] Inventors: William P. Purcell, Memphis, Tenn.; Harlie A. Parish, Jr., Louisville, Ky.

[73] Assignee: Debiopharm SA, Lausanne, Switzerland

[21] Appl. No.: 142,058

[22] PCT Filed: Jan. 10, 1979

[86] PCT No.: PCT/CH79/00003
§ 371 Date: Sep. 17, 1979
§ 102(e) Date: Jul. 19, 1979

[87] PCT Pub. No.: WO79/00517
PCT Pub. Date: Aug. 9, 1979

[30] Foreign Application Priority Data

Jan. 17, 1978 [CH] Switzerland .......................... 472/78

[51] Int. Cl.³ .................... A61K 31/63; A61K 31/24; C07C 143/80; C07C 103/28
[52] U.S. Cl. ............................. 424/228; 260/397.7 R; 424/309; 424/319; 560/21; 560/22; 560/35; 562/435; 562/437; 562/440
[58] Field of Search .................. 564/86; 424/321, 228, 424/309, 319; 260/397.7 R; 560/21, 22, 35; 562/435, 437, 440

[56] References Cited

FOREIGN PATENT DOCUMENTS 599310 1/1960 Belgium ....................... 260/397.7 R
3258M 2/1964 France .
855574 of 0000 France .

OTHER PUBLICATIONS

Smith, T. A. Kilroe et al., *Tetrahedron*, vol. 1, (1957), pp. 38–44.
U.S. Adopted Drug Names; vol. NSB, No. 9, Sep. 1968, p. 511.

*Primary Examiner*—Natalie Trousof
*Assistant Examiner*—L. Hendriksen
*Attorney, Agent, or Firm*—Stevens, Davis, Miller & Mosher

[57] ABSTRACT

Novel therapeutically active derivatives of benzamide, having the general formula

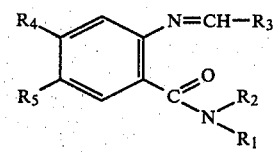

in which $R_1$ and $R_2$, independently of each other, are hydrogen or a lower alkyl group, $R_3$ is a phenyl or lower alkyl or lower alkenyl group, $R_4$ is a halogen or a trifluoromethyl or nitro-group, $R_5$ is a sulphamoyl or carboxyl or carboxy-alkyl group, and the potassium salts of these derivatives.

These compounds are diuretics and hypotensors (blood pressure depressants) and they lower the angiotensin and renin functions, with prolonged action.

5 Claims, 1 Drawing Figure

THERAPEUTICALLY ACTIVE DERIVATIVES OF BENZAMIDE

The present invention relates to novel therapeutically active derivatives of benzamide, having the general formula

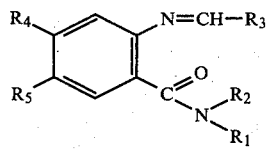

in which $R_1$ and $R_2$, independently of each other, are hydrogen or a lower alkyl group, $R_3$ is a phenyl or lower alkyl or lower alkenyl group, $R_4$ is a halogen or a trifluoromethyl or nitro-group, $R_5$ is a sulphamoyl or carboxyl or carboxy-alkyl group, and the potassium salts of these derivatives.

In this formula, $R_1$ and $R_2$ preferably are a hydrogen atom or a methyl, ethyl, propyl or isopropyl group. $R_3$ is preferably the phenyl group or a methyl, ethyl, vinyl, isopropyl, n-butyl or sec.butyl group. $R_4$ is preferably a halogen, such as chlorine or fluorine, or, possibly, a trifluoromethyl group. $R_5$ preferably is the sulphamoyl group or, possibly, a carboxyl group, which may be esterified by a lower alkanol.

These compounds can be prepared by reacting a compound of the formula

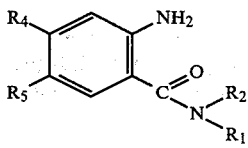

with an aldehyde of the formula $R_3$—CHO. Preferably, this reaction takes place in the presence of zinc chloride, in a solvent, such as toluene, at an elevated temperature not exceeding 175° C. The novel derivatives can exist in the form of alkaline metal salts, for example, in the form of the potassium salt, which takes the place of a hydrogen atom of the sulphamoyl group.

Reference numerals 1 through 9 correspond to those assigned to the formulas of FIG. 1.

EXAMPLE 1

(a) 2.8 g of 2-amino-4-chloro-5-sulphamoylbenzamide are heated under reflux in 125 ml of toluene and 45 ml of dimethylformamide, as solvent, as well as 1.7 g of zinc chloride and 5 ml of benzaldehyde. The solution is heated under reflux for 5 hours and, during this time, the water formed in the course of the reaction is separated by means of a water separator, connected between the reflux condenser and the reaction vessel. After 5 hours, the solvent is expelled by vacuum distillation and 20 ml of ethanol are added to the brown oily residue. After resting overnight, 3.3 g of crude product are collected. Re-crystllisation from a 50:50 mixture of ethanol and water gives 2.4 g (64%) of 2-N-(benzylidene-amino)-4-chloro-5-sulphamoylbenzamide, which melts at 220–230° C. and solidifies at 260–280° C., according to the velocity of heating.

(b) 0.5 g of this product is added to 4.7 ml of absolute ethanol, containing 0.017 g/ml of potassium hydroxide. The solution is evaporated to dryness in vacuo, to obtain 0.4 g of the potassium salt of 2-N-(benzylidene-amino)-4-chloro-5-sulphamoylbenzamide.

The IR*spectrum of the product obtained according to (a) above shows a maximum at 1620 cm$^{-1}$ for the —N=CH-group, while the UVspectrum shows a maximum at 279 nm. The *NMR-spectrum shows adsorptions (sic!) at 5.7 ppm (1 proton), 6.6 ppm (1 proton), 7.3 ppm (5 protons) and 8.2 ppm (1 proton).

*infra-red ultraviolet *nuclear magnetic resonance

EXAMPLE 2

2-acetamido-4-fluorotoluene (2)

139 ml (150.4 g; 1.473 molecules) of acetic anhydride were added in one portion to a hot (35°) stirred mixture of 90.0 g (0.719 molecule) of 2-amino-4-fluorotoluene (1) in 513 ml of water. The temperature rose to 73° and a solid separated out (by precipitation). The mixture was cooled to ambient temperature and the solid was recovered on a filter, washed with water (525 ml), then dried in vacuo at 80°, yield: 115.7 g (96.2%); m.p.: 127°–128°. The material was still transformable.

2-acetamido-4-fluoro-5-sulphamyltoluene (4)

95.7 g (0.572 molecule) of 2-acetamido-4-fluorotoluene (2) were added, in portions, to 190 ml (340.1 g; 2.920 molecules) of chlorosulphonic acid, kept between 0° and 20° with an ice-acetone bath in dry state. The bath was withdrawn and 31.7 g (0.543 molecule) of sodium chloride were slowly added. Marked effervescence of hydrogen chloride was observed. The reaction did not appear to be exothermic. The mixture was slowly heated until it reached 50° and kept at that temperature for 3.75 hours. The hot mixture was poured into a thoroughly stirred mixture of 600 ml of water and of 400 g of ice. CARE: Chlorosulphonic acid vigorously reacts with water. The solid, which separated out, was recovered on a filter, washed with water (500), then used in the following reaction.

The moist 2-acetamido-4-fluoro-5-chlorosulphonyl-toluene (3) was heated in 650 ml of concentrated ammonium hydroxide until it reached 50°. The resulting solution was cooled and extracted with ethyl acetate, (10×1000 ml). The extracts were combined and concentrated in vacuo, to give a solid. The latter was purified by dissolving the solid in 350 ml of a 20% aqueous solution of sodium hydroxide, filtering this mixture and acidifying the filtrate with concentrated hydrochloric acid. The precipitate, which separated out, was recovered, then dried; yield: 32.9 g (23.4%); m.p.: 205–207°; literature:[1] m.p.: 206–208°.

4-fluoro-5-sulphamylanthranilic acid (6)

A mixture of 25.0 g (0.102 molecule) of purified sulphonamide (4), 36.7 g of magnesium sulphate heptahydrate and of 560 ml of water was stirred and heated to 80°. Potassium permanganate (48.1 g) was added, in portions, keeping the temperature between 80° and 85°. The mixture was taken to 90° during 4 hours, filtered hot and the cake, (collected into a mass), of manganese dioxide was washed with water. The filtrate was acidified with concentrated hydrochloric acid and the precipitate of compound 5 was recovered. The moist compound 5 of the above reaction and 4.0 g., previously obtained, were heated under reflux for three hours in 215 ml of 3N sodium hydroxide. The reaction mixture was filtered and the filtrate was acidified with concentrated hydrochloric acid. The separating solid was recovered on a filter, washed with water, then dried in vacuo at 80°; yield: 20.1 g (70.5%).

Methyl 2-amino-4-fluoro-5-sulphamylbenzoate (7)

A reaction flask, containing 7.2 g (0.0307 molecule) of 4-fluoro-5-sulphamylanthranilic acid (6) in 125 ml of methanol and 10 ml of concentrated sulphuric acid, was attached to a Soxhlet apparatus, containing molecular sieves 4A, immersed in methanol (25 ml). After 48 hours' reflux, the solution was poured into cold water (500 ml), containing 25 g of potassium carbonate. The solid, which separated out, was recovered on a filter and dried in vacuo at 80°; yield: 5.6 g (73.7%); m.p.: 209°–211°.

2-amino-4-fluoro-5-sulphamylbenzamide (8)

A mixture of 4.8 g (0.0193 molecule) of methyl 2-amino-4-fluoro-5-sulphamylbenzoate (7) in 75 ml of concentrated ammonium hydroxide was taken to 50°, to obtain complete solution. The solution was cooled and returned to ambient temperature, diluted with a fresh solution of 75 ml of concentrated ammonium hydroxide and allowed to rest for 65 hours. It was extracted with ethyl acetate (1×250 ml; 4×500 ml) and the extracts were combined, dried over anhydrous magnesium sulphate and concentrated in vacuo, to give a solid. The latter was ground with 25 ml of ethyl acetate, to give 2.7 g (60.0%) of pure product (8).

The anthranilic acid (6) was recovered by acidifying the ammonium hydroxide layer with concentrated hydrochloric acid; recovered: 0.8 g of acid (6).

2-N-(benzylidene-amino)-4-fluoro-5-sulphamylbenzamide (9)

A mixture of 5.4 g (0.0232 molecule) of the amide (8), of 3.5 ml of benzaldehyde and of 3.2 g of zinc chloride in 75 ml of toluene and 30 ml of N,N-dimethylformamide was heated under reflux for 26 hours, the water being removed. The solvent was taken off in vacuo and the oily, reddish-brown residue was dissolved in 25 ml of a 75% aqueous solution of ethanol/and then heated under reflux for 15 minutes. The solution was cooled, while being stirred, throughout the night and the solid, which separated out, was analytically pure; yield: 3.2 g (43.2%); m.p.: 223°–243°, with re-solidification.

Additional material was obtained by concentrating the mother liquor with 20 g of colloidal silica and by placing it on top of a colloidal silica column (35 cm × 4 cm). Extraction was carried out with dichloromethane (450 ml), dichloromethane/ethyl acetate (1:1) (1050 ml) and then ethyl acetate (600 ml). Fractions (of 75 ml each), containing the product according to thin layer chromatographic determination, were combined, concentrated in vacuo and then dissolved in 60 ml of ethanol and diluted with 45 ml of water. The solid, which separated out, was recovered and dried; yield: 1.4 g (18.9%).

The compounds according to the invention, and particularly that according to the claims 2 and 3, are diuretics and anti-hypertensors (blood pressure depressants); moreover, they have an antagonistic action on angiotensin and renin. The action of these compounds is prolonged in time, so that their action remains effective for a period of from 6 to 12 hours, according to the doses.

The acute toxicity, LD50, of the product according to the claims 2 and 3 is below 2.4 g/kg, orally administered, and 3.0 g/kg, intraperitoneally administered, in mice, while the effective dose, DE50, is about 0.13 mg/kg. For the treatment in the case of humans, doses of from 10 to 60 mg per day, in one or several doses, will be used.

The compounds according to the invention can be administered in any galenic (pharmaceutical) form, for example, in the form of tablets, capsules, gelatine-coated pills, suppositories and intravenous or intramuscular solutions.

We claim:

1. A therapeutically active benzamide having the formula

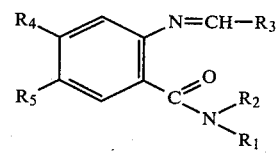

in which $R_1$ and $R_2$, independently of each other, are hydrogen or a lower alkyl group, $R_3$ is a phenyl or lower alkyl or lower alkenyl group, $R_4$ is a halogen or a trifluoromethyl or nitro-group, $R_5$ is a sulphamoyl or carboxyl or carboxy-alkyl group, and the potassium salts of said derivative.

2. The compound, 2-n-benzylideneamino-4-chloro-5-sulphamoyl benzamide, having the formula

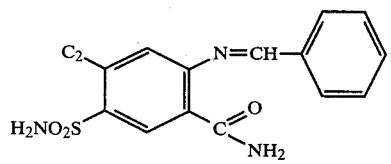

as well as the potassium salts thereof.

3. The compound, 2-n-benzylideneamino-4-fluoro-5-sulphamoyl benzamide, having the formula

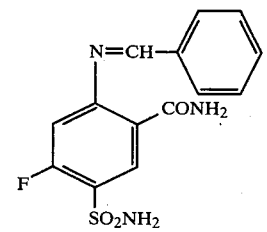

as well as the potassium salts thereof.

4. A therapeutically active benzamide having the formula

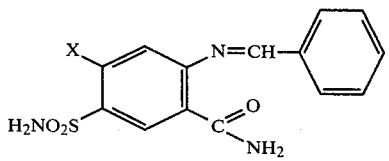

in which X is selected from the group of chlorine and fluorine, as well as the potassium salts thereof.

5. A pharmaceutical composition having diuretic and antipyretic activity, said composition comprising a pharmaceutically acceptable carrier and a pharmaceutically active quantity of a compound according to claim 1 or 4.

* * * * *

UNITED STATES PATENT AND TRADEMARK OFFICE
CERTIFICATE OF CORRECTION

PATENT NO. : 4,312,862
DATED : January 26, 1982
INVENTOR(S) : William Paul PURCELL, et al.

It is certified that error appears in the above—identified patent and that said Letters Patent is hereby corrected as shown below:

In claim 2, in the structural formula, change "$C_2$" to -- Cl --.

In item 56 of the cover page, change "3258M" to -- 3528M --.

Signed and Sealed this

Fourteenth Day of December 1982

[SEAL]

Attest:

Attesting Officer

GERALD J. MOSSINGHOFF
Commissioner of Patents and Trademarks